(12) United States Patent
Bauer et al.

(10) Patent No.: US 9,096,973 B2
(45) Date of Patent: Aug. 4, 2015

(54) METHOD FOR REGULATING THE FORMATION OF A FIBROUS WEB

(71) Applicant: Voith Patent GmbH, Heidenheim (DE)

(72) Inventors: Armin Bauer, St. Pölten (AT); Jürgen Käser, Wolfegg (DE); Alexander Wohlmuth, Schorndorf (DE); Jens Haag, Heidenheim (DE); Christian Naydowski, Wikon (CH); Martin Staiger, Westerstetten (DE); Günther Kriechbaum, Weingarten (DE); Herbert Britz, Berg (DE)

(73) Assignee: Voith Patent GmbH, Heidenheim (DE)

( * ) Notice: Subject to any disclaimer, the term of this patent is extended or adjusted under 35 U.S.C. 154(b) by 0 days.

(21) Appl. No.: 13/847,769

(22) Filed: Mar. 20, 2013

(65) Prior Publication Data

US 2013/0213596 A1   Aug. 22, 2013

Related U.S. Application Data

(63) Continuation of application No. PCT/EP2011/065940, filed on Sep. 14, 2011.

(30) Foreign Application Priority Data

Sep. 20, 2010 (DE) .......................... 10 2010 041 052

(51) Int. Cl.
    *D21F 11/00*   (2006.01)
    *D21G 9/00*    (2006.01)
    *G01N 33/34*   (2006.01)

(52) U.S. Cl.
    CPC .............. *D21F 11/00* (2013.01); *D21G 9/0027* (2013.01); *G01N 33/343* (2013.01)

(58) Field of Classification Search
    CPC ....... D21H 17/00; D21H 23/04; D21H 23/24; D21H 21/10; Y10S 162/06; Y10S 162/10; Y10S 162/11; D21G 9/0027; D21G 9/0009; G01N 33/343; D21F 11/00; D21F 1/0009; D21F 1/08
    USPC .................. 162/198, 158, 164.1, 168.1, 175, 162/DIG. 6, DIG. 10, DIG. 11, 192; 700/127–129
    See application file for complete search history.

(56) References Cited

U.S. PATENT DOCUMENTS

3,547,775 A * 12/1970 Bossen et al. .................. 162/198
3,576,713 A *  4/1971 Fricke ............................ 162/198

(Continued)

FOREIGN PATENT DOCUMENTS

DE          101 18 508  A1   10/2002
DE    10 2005 062 304  A1    6/2007

(Continued)

OTHER PUBLICATIONS

Internationaler Recherchenbericht dated Nov. 17, 2011 and Schriftlicher Bescheid Der Internationalen Rechercenbehoerde for PCT/EP2011/065940 (10 pages).

(Continued)

*Primary Examiner* — Jose Fortuna
(74) *Attorney, Agent, or Firm* — Taylor IP, P.C.

(57) ABSTRACT

A method regulating the formation of a fibrous web, such as a paper, cardboard, or tissue web, in which method the formation of the fibrous web is measured online as a controlled variable and is held at a predefinable setpoint level via automatic formation regulation. In addition to the formation, the charge concentration of the suspension is measured as a controlled variable and is taken into consideration during the formation regulation.

13 Claims, 2 Drawing Sheets

(56) References Cited

U.S. PATENT DOCUMENTS

| | | | |
|---|---|---|---|
| 4,535,285 A * | 8/1985 | Evans et al. | 324/71.1 |
| 5,202,016 A * | 4/1993 | Church et al. | 210/85 |
| 5,314,581 A * | 5/1994 | Lin et al. | 162/263 |
| 5,365,775 A * | 11/1994 | Penniman | 73/53.04 |
| 5,373,229 A * | 12/1994 | Penniman | 324/71.1 |
| 5,393,378 A * | 2/1995 | Yakabe et al. | 162/61 |
| 5,549,793 A * | 8/1996 | Hellstrom et al. | 162/258 |
| 5,680,321 A * | 10/1997 | Helmer et al. | 702/30 |
| 6,076,022 A * | 6/2000 | Hagart-Alexander et al. | 700/127 |
| 6,176,974 B1 | 1/2001 | Hubbe | |
| 6,805,772 B2 * | 10/2004 | Schwarz | 162/198 |
| 6,993,408 B2 * | 1/2006 | Puurtinen | 700/128 |
| 7,566,382 B2 * | 7/2009 | Hietaniemi | 162/198 |
| 8,253,791 B2 * | 8/2012 | Gruber-Nadlinger et al. | 348/86 |
| 2002/0179268 A1 * | 12/2002 | Schwarz | 162/198 |
| 2003/0205347 A1 * | 11/2003 | Shead et al. | 162/198 |
| 2004/0238140 A1 * | 12/2004 | Laitinen-Vellonen | 162/198 |
| 2005/0224204 A1 * | 10/2005 | Hietaniemi | 162/198 |
| 2005/0279477 A1 * | 12/2005 | Hietaniemi | 162/198 |
| 2007/0158044 A1 | 7/2007 | Jaschinski et al. | |
| 2009/0033743 A1 * | 2/2009 | Gruber-Nadlinger et al. | 348/86 |
| 2009/0220146 A1 * | 9/2009 | Bauer et al. | 382/159 |
| 2013/0213596 A1 * | 8/2013 | Bauer et al. | 162/164.3 |

FOREIGN PATENT DOCUMENTS

| | | |
|---|---|---|
| DE | 102007047843 A1 * | 5/2009 |
| DE | 102007055833 A1 * | 6/2009 |
| DE | 102010041052 A1 * | 3/2012 |
| EP | 1 342 843 A1 | 9/2003 |
| EP | 2096578 A2 * | 9/2009 |
| WO | WO 2007090724 A1 * | 8/2007 |
| WO | WO 2012038310 A1 * | 3/2012 |

OTHER PUBLICATIONS

English translation of International Search Report dated Nov. 17, 2011 for PCT/EP2011/065940 (2 pages).

English translation of Written Opinion of the International Searching Authority (undated) for PCT/EP2011/065940 (7 pages).

Martin A. Hubbe and Junjua Chen; Streaming Current Measurements; Charge-Related Measurement—A Reappraisal. Part 1. Streaming Current; Paper Technology; Oct. 2004; North Carolina State University, Dept. of Wood and Paper Science; pp. 17-23.

A. Elisabet Horvath; Appropriate Conditions for Polyelectrolyte Titration to Determine the Charge of Cellulosic Fibers; Kungl Tekniska HOgskolan; Stockholm 2003; Royal institute of Technology (39 pages).

* cited by examiner

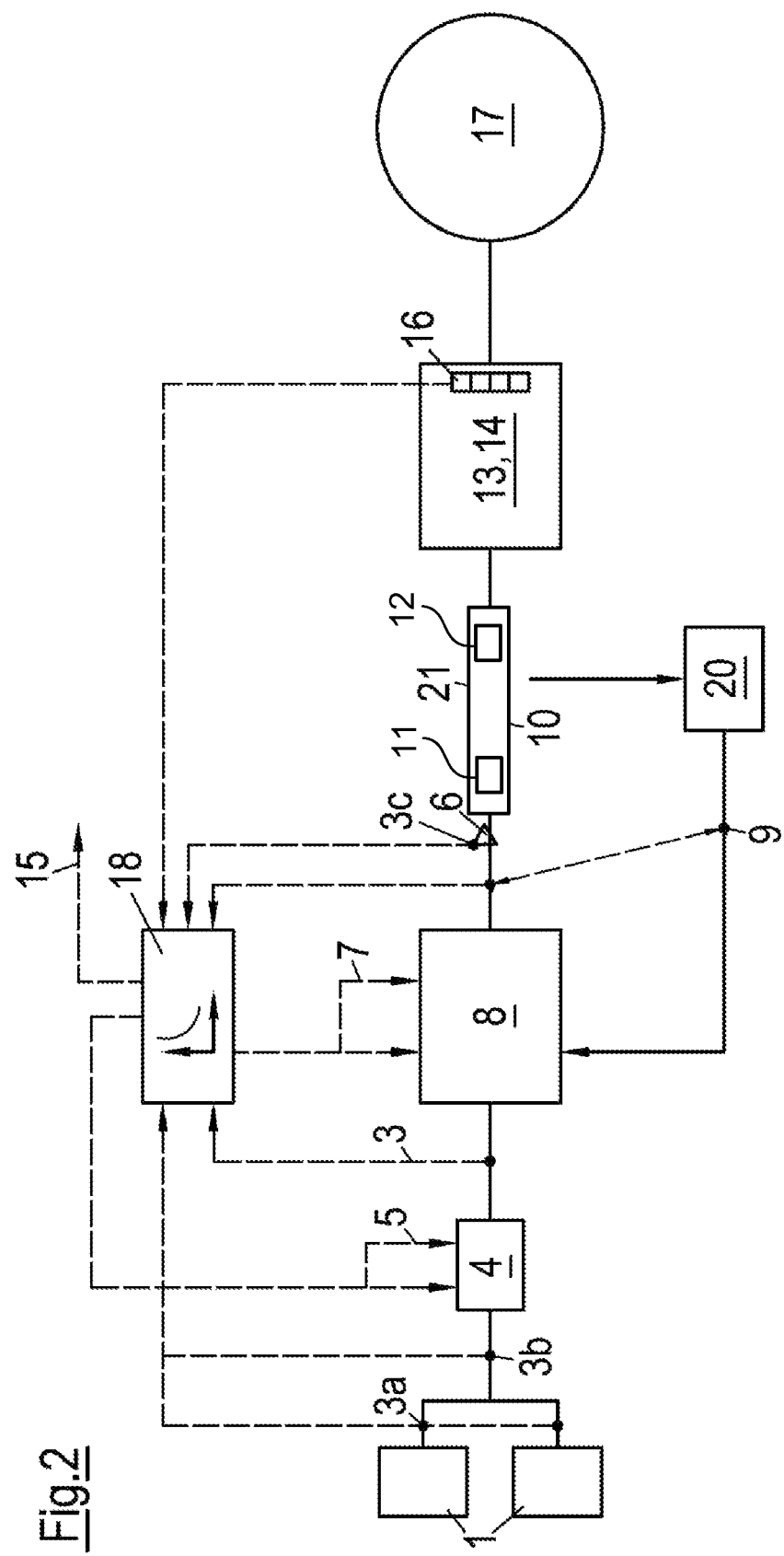

9,096,973 B2

METHOD FOR REGULATING THE FORMATION OF A FIBROUS WEB

CROSS REFERENCE TO RELATED APPLICATIONS

This is a continuation of PCT application No. PCT/EP2011/065940, entitled "METHOD FOR REGULATING THE FORMATION OF A FIBROUS WEB", filed Sep. 14, 2011, which is incorporated herein by reference.

BACKGROUND OF THE INVENTION

1. Field of the Invention

The invention relates to a method as well as to a device for regulating the formation of a fibrous web, in particular a paper, cardboard or tissue web, whereby formation of the fibrous web is measured online as a control variable and is kept to a predefined set point level via automatic formation control.

2. Description of the Related Art

The fiber distribution and composition in a fibrous web is described as formation. The formation is generally also described as the "look-through" for example of the paper.

Inspection and evaluation of the formation generally occurs in that the paper is X-rayed. The structure and the level of uniformity of the fiber distribution in the paper is a measure for the formation. A distinction is hereby made between uniform, placid and clear look-through for paper of good quality and irregular, cloudy and very unsettled look-through for lesser quality papers.

The formation of a paper or cardboard web is a decisive quality characteristic which influences the further processing of the fibrous web in a multifaceted way. One example is the influence of the formation on the strength and the printability of the end product.

The formation of a paper or cardboard web is influenced on the one hand by the raw material used and on the other hand to a not inconsiderable extent by the sheet formation. The sheet formation is hereby determined by the headbox and the forming unit. The forming unit may for example comprise a Fourdrinier or a hybrid former or a modern twin wire former.

The values which influence the formation in this process step may for example be stock consistency, vacuums in the forming unit, the retention and the water volume, as already also described in DE 10 2005 062 304 A1.

Experience shows that even minor changes in the composition and the characteristics of the used fibrous stock can have considerable influence on the formation. Moreover, each change in basis weight of a paper web requires readjustment of the values influencing the formation.

Because of these aforementioned reasons the formation is subject to continuous fluctuations. These formation fluctuations are especially pronounced in products containing waste paper, which can be ascribed to the corresponding fluctuations in the raw material composition.

Today, spontaneously occurring formation changes are countered mainly through mechanical adjustment of the headbox lip opening. This alters the stock consistency in the infeed to the headbox, so that the basis weight can be kept constant.

In order to improve the formation an enlargement of the lip opening is necessary, leading to higher energy use, since the throughput volume is increased. As a result however, the overall ash-retention decreases disadvantageously, requiring the addition of more retention agents.

Also affected are the control circuits for automatic dosing of retention agents, as well as the efficiency of the white water filtering downstream units.

The drop in retention makes the addition of increased volumes of retention agents necessary, thereby also negatively impacting the formation due to stronger flocculation. A process fluctuation is released by these self-exciting control circuits which destabilizes the entire water management system of the paper machine (stock metering station, approach flow system, process water recovery, stock preparation) over several hours.

To automatically control the formation, several online formation measurements and controls are disclosed in the current state of the art, for example in EP 1 342 843 A1, DE 101 18 508 A1 or DE 10 2005 062 304 A1. It is for example suggested to keep the formation to a predefinable setpoint level with the assistance of the dewatering efficiency in the forming unit or by means of the retention agent adjustment.

What is needed in the art is to create an improved method as well as an improved apparatus of the type described at the beginning with which the formation of a fibrous web can be stabilized at a higher level.

SUMMARY OF THE INVENTION

The present invention provides a method of controlling the formation of a fibrous web, such as a paper, cardboard or tissue web, whereby the formation of the fibrous web is measured online as a controlled variable and is held at a predefinable setpoint level via automatic formation control, characterized in that in addition to the formation the charge concentration of the fibrous suspension forming the fibrous web is measured as a controlled variable and is taken into consideration during formation control.

The present invention provides an apparatus to produce a fibrous web, such as a paper, cardboard or tissue web including a formation sensor with which the formation of the fibrous web is measured online as a controlled variable and is adjusted by means of an automatic formation control to a predefinable setpoint level, characterized in that a charge concentration sensor 3, 3a, 3b, 3c for charge concentration measurement is provided with which the charge concentration is measured as a controlled variable and is taken into consideration in formation control.

According to the invention it is suggested to improve the method of controlling the formation of a fibrous web, such as a paper, cardboard or tissue web in such a manner that not only the formation of the fibrous web is measured online as a controlled variable and is held at a predefinable setpoint level via automatic formation control but that, in addition to the formation, the charge concentration of the fibrous suspension forming the fibrous web is measured as a controlled variable and is taken into consideration during formation control.

The charge concentration or charge requirement is measured in the fluid phase of the fibrous suspension.

The formation can hereby be determined directly via at least one formation sensor and/or indirectly via at least one auxiliary quantity, in particular the water volumes in the forming unit. A direct formation measurement can for example occur by means of a camera.

The charge concentration can for example be determined through an automated polyelectrolyte-titration.

One arrangement of the invention provides for measuring the charge concentration continuously and online, so that each change in the charge concentration can be directly controlled. However, an intermittent measurement is also conceivable, for example when no great fluctuations are expected. Moreover, an offline measurement is also conceivable.

A machine to produce a fibrous web consists essentially of a raw stock preparation section, a raw stock mixing device, a sheet forming section, a sheet drying section, a sheet converting section and a winding device which are arranged in succession in the direction of production. Measuring of the charge concentration occurs preferably at one or several locations before the sheet forming section.

In one advantageous design variation the measurement of the charge concentration is performed before the approach flow section or respectively after the raw material mixing device. The effect of the individual process chemicals on the formation is thereby determinable.

Moreover, measurement of the charge concentration can occur before or after addition of fixing agents, viewed in direction of production. The effect of the fixing agent on the suspension can hereby be determined especially advantageously and thereby addition of the fixing agent is able to be optimized.

Another alternative of improving the formation control is to measure the charge concentration before and after the addition of retention agents, viewed in production direction. This allows for the effect of the retention agent upon the charge concentration to be evaluated and to be utilized for the improvement of the formation and/or to control the retention agent addition.

For controlling the formation and/or charge concentration it is suggested according to the invention to hold one or several manipulated variables to a predefined setpoint level through appropriate changing of said manipulated variables Since the formation and the charge concentration depend on a great many factors, they can be held to a predefinable setpoint level by targeted changing of one or several of the following manipulated variables:

fixing agent addition
retention agent addition
freeness value
mass starch addition
composition of stock mixture
sizing agent addition (resin size, AKD, ASA, polyvinyl amine)
wet strength agent addition (melamine-formaldehyde condensate, urea-formaldehyde condensate, epichlorohydrin, etc.)
vacuum at the forming roll
vacuum at the forming shoe
position of the dewatering elements in the wire section
lip opening
fresh water addition.

Through the additional measurement of the charge concentration it is possible to change one of the manipulated variables more specifically without lastingly destabilizing the control circuit for the formation control. The regulating range of the manipulated variables can hereby be limited within a predefinable range.

When reaching at least one of the predefinable limits of a regulating range of at least one of the manipulated variables an alarm is triggered.

A preferred practical design variation of the inventive apparatus to produce a fibrous web, such as a paper, cardboard or tissue web comprises a formation sensor with which the formation of the fibrous web is measured online as a controlled variable and is adjusted by means of a formation control to a predefinable setpoint level, whereby a charge concentration sensor for charge concentration measurement is provided with which the charge concentration is measured as a controlled variable and is taken into consideration in formation control.

The formation is measured in the apparatus with a formation sensor, for example a camera, and the charge concentration with a charge analyzer, whereby these measurements are supplied to the formation controller. The formation controller may for example be a PID controller.

In view of the complexity of the inter-relations in a formation control it is in particular also advantageous if the apparatus includes at least one status controller and/or at least one controller with at least one self-learning control algorithm.

Viewed in production direction it is advantageous if charge concentration sensors are provided in the apparatus at one or several locations prior to the former. A charge concentration sensor is preferably installed before the approach flow system or respectively after the raw material mixing device.

To increase the dynamic of the control circuit it is moreover advantageous if a charge concentration sensor is provided after and/or before the raw material mixing device, so that fluctuations in the charge concentration which are caused by the addition of fixing agents into the raw material mixing device may be responded to immediately.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 2 is a schematic illustration of the control system of another design variation of the apparatus according to the invention for the production of a fibrous web, with expanded automatic control.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
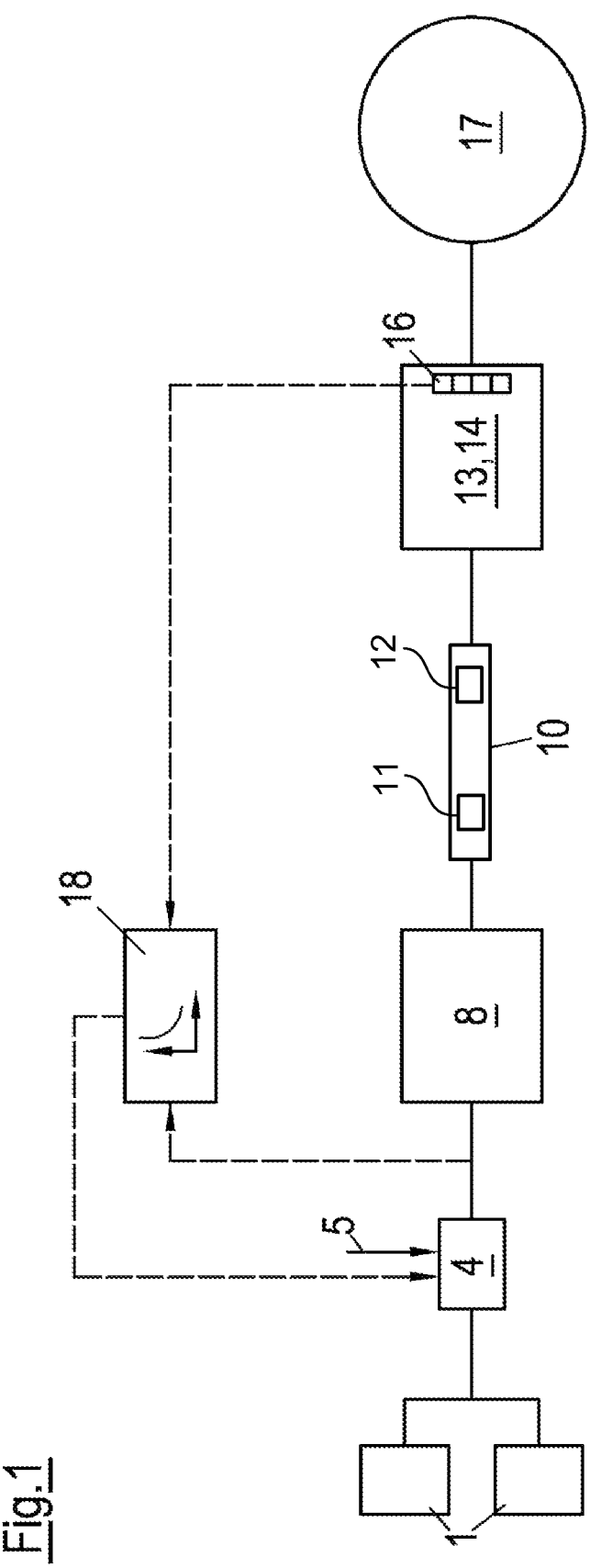
FIG. 1 is a schematic illustration of one design variation of the apparatus according to the invention for the production of a fibrous web with controlled formation.

FIG. 1 is a schematic illustration of an exemplary design variation of an inventive apparatus for the production of a fibrous web which may in particular be a paper, cardboard or tissue web.

Referring now to FIG. 1, the apparatus comprises a stock preparation section with a raw material mixing device 4, an approach flow system 8, a sheet forming and dewatering and dewatering section 10, 11, a sheet drying section 13 and a converting section 14 and a formation controller 18 to control the formation.

Formation of the fibrous web is measured online as a controlled variable via a measuring device 16 which is provided at the end of the sheet drying section 13 and converting section 14. This occurs for example through a camera system according to the current state of the art. The charge concentration in the fibrous suspension is measured online with a charge analyzer after raw material mixing 4. Both values—formation and charge concentration—are supplied to the formation controller 18 as controlled variables.

Formation can be held to a predefinable setpoint level via the automatic formation controller 18, whereby the addition of fixing agent into the raw material mixing device 4 is controlled via formation controller 18. Additional controlled variables as listed above can moreover be changed in order to control the formation process, whereby these are not illustrated.

FIG. 2 shows a schematic illustration of the control system in another design variation of the inventive apparatus for the production of a fibrous web, with expanded controls for controlling the formation.

An expanded control unit includes additional charge concentration sensors 3a, 3b, 3c and in addition, retention 9 is measured online and is supplied as a controlled variable to the formation control.

Formation control therefore does not only occur based on one measurement and the change in the fixing agent addition but, due to several charge concentration measurements there is now the possibility to optimize the formation control at various locations in the suspension preparation before former 12 and retention measurement 9 insofar that the addition of fixing agent as wells as the addition of retention agent can be minimized.

For further improvements other controlled variables and adjustments as discussed above can be changed through the formation control.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

COMPONENT IDENTIFICATION LIST

1 Raw materials
3, 3a, 3b, 3c Charge measuring point
4 Raw material mixing
5 Fixing agent
6 Headbox
7 Retention agent
8 Approach flow section
9 Retention measurement
10 Sheet formation
11 Dewatering
12 Former
13 Sheet drying
14 Converting
15 to other controlled variable controllers
16 Formation measuring
17 Winding
18 Formation controller
20 White water circuit
21 Dewatering sensor

What is claimed is:

1. A method of controlling a formation of a web of fibrous material, said method comprising the steps of:
measuring online the formation of the web as a controlled variable;
holding the formation of the web at a predefinable setpoint level via an automatic formation control;
measuring, in addition to the formation, a charge concentration of a fibrous suspension forming the web as a controlled variable and taking into consideration said charge concentration during said formation control, wherein said charge concentration is held to a predefined setpoint level through appropriate changing of at least one manipulated variable.

2. The method according to claim 1, wherein the web is one of a paper web, a cardboard web, and a tissue web.

3. The method according to claim 1, wherein the formation is determined at least one of (a) directly via at least one formation sensor and (b) indirectly via at least one auxiliary quantity.

4. The method according to claim 3, wherein said at least one auxiliary quantity is at least one water volume in a forming unit.

5. The method according to claim 1, wherein said charge concentration is measured by way of a charge analyzer.

6. The method according to claim 1, wherein said step of measuring said charge concentration occurs one of continuously and intermittently, one of online and offline.

7. The method according to claim 1, wherein said step of measuring said charge concentration occurs at at least one location before a sheet forming section, viewed in a direction of production.

8. The method according to claim 1, wherein said step of measuring said charge concentration is performed one of before an approach flow section and respectively after a raw material mixing device.

9. The method according to claim 8, wherein said step of measuring said charge concentration occurs one of before and after adding a plurality of fixing agents, viewed in a direction of production.

10. The method according to claim 1, wherein said step of measuring said charge concentration occurs one of before and after adding a plurality of retention agents, viewed in a direction of production.

11. The method according to claim 1, wherein at least one of the following manipulated variables is appropriately changed: a fixing agent addition; a retention agent addition; a freeness value; a composition of a stock mixture; a mass starch addition; a sizing agent addition; a wet strength agent addition; a vacuum at a forming roll; a vacuum at a forming shoe; a position of a plurality of dewatering elements in a wire section; and a lip opening.

12. The method according to claim 11, wherein said sizing agent addition includes at least one of resin size, AKD, ASA, and polyvinyl amine.

13. The method according to claim 11, wherein said wet strength agent addition includes at least one of melamine-formaldehyde condensate, urea-formaldehyde condensate, and epichlorohydrin.

* * * * *